US011167005B2

(12) United States Patent
Mozes

(10) Patent No.: US 11,167,005 B2
(45) Date of Patent: Nov. 9, 2021

(54) PEPTIDES FOR TREATING SJOGREN'S SYNDROME

(71) Applicant: YEDA RESEARCH AND DEVELOPMENT CO. LTD., Rehovot (IL)

(72) Inventor: Edna Mozes, Revohot (IL)

(73) Assignee: YEDA RESEARCH AND DEVELOPMENT CO. LTD., Rehovot (IL)

(*) Notice: Subject to any disclaimer, the term of this patent is extended or adjusted under 35 U.S.C. 154(b) by 0 days.

(21) Appl. No.: 16/474,831

(22) PCT Filed: Jan. 4, 2018

(86) PCT No.: PCT/IL2018/050012
§ 371 (c)(1),
(2) Date: Jun. 28, 2019

(87) PCT Pub. No.: WO2018/127914
PCT Pub. Date: Jul. 12, 2018

(65) Prior Publication Data
US 2019/0351004 A1    Nov. 21, 2019

Related U.S. Application Data

(60) Provisional application No. 62/442,441, filed on Jan. 5, 2017, provisional application No. 62/481,702, filed on Apr. 5, 2017, provisional application No. 62/557,153, filed on Sep. 12, 2017.

(51) Int. Cl.
| | |
|---|---|
| A61K 38/04 | (2006.01) |
| A61K 38/10 | (2006.01) |
| A61P 11/00 | (2006.01) |
| A61P 15/00 | (2006.01) |
| A61P 17/00 | (2006.01) |
| A61P 17/16 | (2006.01) |
| A61P 19/02 | (2006.01) |
| A61P 1/02 | (2006.01) |
| A61P 27/02 | (2006.01) |
| A61P 37/02 | (2006.01) |
| A61P 43/00 | (2006.01) |
| C07K 7/08 | (2006.01) |

(52) U.S. Cl.
CPC .............. *A61K 38/04* (2013.01); *A61P 43/00* (2018.01)

(58) Field of Classification Search
CPC ......... A61K 38/04; A61K 38/10; A61P 11/00; A61P 15/00; A61P 17/00; A61P 17/16; A61P 19/02; A61P 1/02; A61P 27/02; A61P 37/02; A61P 43/00; C07K 7/08
USPC ........ 514/1.1, 7.1, 11.1, 21.4; 530/300, 326, 530/311
See application file for complete search history.

(56) References Cited

U.S. PATENT DOCUMENTS

| | | | |
|---|---|---|---|
| 6,613,536 B1 | 9/2003 | Edna | |
| 7,294,687 B2 | 11/2007 | Sharon | |
| 2007/0086979 A1* | 4/2007 | Chevrier | A61P 19/02 424/85.1 |
| 2018/0043016 A1 | 2/2018 | Urowitz | |
| 2018/0043017 A1 | 2/2018 | Urowitz | |

FOREIGN PATENT DOCUMENTS

| | | |
|---|---|---|
| WO | 02067848 A2 | 9/2002 |
| WO | 2004064787 A2 | 8/2004 |
| WO | 2008087647 A2 | 7/2008 |
| WO | 2014052393 A2 | 4/2014 |

OTHER PUBLICATIONS

Sjogren's Syndrome from Mayo Clinic, pp. 1-5. Accessed Apr. 27, 2020. (Year: 2020).*
Siegel-Itzkovich, "Weizmann professor is not afraid of the big bad wolf," The Jerusalem Post, Mar. 30, 2014, pp. 1-5. (Year: 2014).*
Edratide from PubChem, https://pubchem.ncbi.nih.gov/compound/Edratide, pp. 1-20, Accessed Dec. 10, 2020. (Year: 2020).*
Martins, Ines; "HCDR1 Therapy Has Positive Impact on Sjogren Syndrome as Well as Lupus, Its Maker XTL Reports," Lupus News Today, Apr. 5, 2017, pp. 1-7. (Year: 2017).*
Almeida González et al., (2015) Anti-dsDNA antibodies in systemic lupus erythematosus: A combination of two quantitative methods and the ANA pattern is the most efficient strategy of detection. J Immunol Methods 427: 30-35.
Brito-Zerón et al., (2016) Sjögren syndrome. Nat Rev Dis Primers 2:16047; 20 pages.
Koski et al., (2001) Tumor necrosis factor-alpha and receptors for it in labial salivary glands in Sjögren's syndrome. Clin Exp Rheumatol 19(2): 131-137.
Li et al., (2007) T regulatory cells are markedly diminished in diseased salivary glands of patients with primary Sjögren's syndrome. The Journal of Rheumatology December 34(12): 2438-2445.
Liu et al., (2008) Decreased CD4+CD25+bright T cells in peripheral blood of patients with primary Sjögren's syndrome. Lupus 17(1): 34-39.
Maria et al., (2014) MxA as a clinically applicable biomarker for identifying systemic interferon type I in primary Sjögren's syndrome. Ann Rheum Dis 73(6): 1052-1059.

(Continued)

*Primary Examiner* — Julie Ha
(74) *Attorney, Agent, or Firm* — J.A. Lindeman & Co., PLLC

(57) ABSTRACT

Compositions and methods for the treatment of Sjogren's syndrome (SS) and SS-related symptoms in human subjects are described. The compositions comprise synthetic peptides based on the sequence of CDR1 of an anti-DNA monoclonal antibody.

11 Claims, 4 Drawing Sheets

Specification includes a Sequence Listing.

(56) References Cited

OTHER PUBLICATIONS

Maria et al., (2016) Association of Increased Treg Cell Levels With Elevated Indoleamine 2,3-Dioxygenase Activity and an Imbalanced Kynurenine Pathway in Interferon-Positive Primary Sjögren's Syndrome. Arthritis Rheumatol 68(7): 1688-1699.

Mariette et al., (2003) The level of BLyS (BAFF) correlates with the titre of autoantibodies in human Sjögren's syndrome. Ann Rheum Dis 62(2): 168-171.

Mozes and Sharabi (2010) A novel tolerogenic peptide, hCDR1, for the specific treatment of systemic lupus erythematosus. Autoimmun Rev 10(1): 22-26.

Park et al., (2015) Mouse Models of Primary Sjogren's Syndrome. Curr Pharm Des 21(18): 2350-2364.

Patel and Shahane (2014) The epidemiology of Sjögren's syndrome. Clin Epidemiol 6: 247-255.

Rao and Bowman (2013) Latest advances in connective tissue disorders. Ther Adv Musculoskelet Dis 5(4): 234-249.

Riega-Torres et al., (2016) Sjögren's syndrome (SS), a review of the subject and saliva as a diagnostic method. Gac Med Mex 152(3): 371-380 abstract.

Scofield et al., (2005) Immunization with short peptides from the 60-kDa Ro antigen recapitulates the serological and pathological findings as well as the salivary gland dysfunction of Sjögren's syndrome. J Immunol 175(12): 8409-8414.

Sthoeger et al., (2009) The tolerogenic peptide hCDR1 downregulates pathogenic cytokines and apoptosis and upregulates immunosuppressive molecules and regulatory T cells in peripheral blood mononuclear cells of lupus patients. Hum Immunol 70(3): 139-145.

Sthoeger et al., (2013) The tolerogenic peptide, hCDR1, downregulates the expression of interferon-$\alpha$ in murine and human systemic lupus erythematosus. PLoS One 8(3): e60394; 8 pages.

Urowitz et al., (2015) Safety and efficacy of hCDR1 (Edratide) in patients with active systemic lupus erythematosus results of phase II study. Lupus Sci Med 2(1): e000104; 11 pages.

Willeke et al., (2003) Interleukin 1beta and tumour necrosis factor alpha secreting cells are increased in the peripheral blood of patients with primary Sjögren's syndrome Ann Rheum Dis 62(4): 359-362.

Yu et al., (2013) DNA hypermethylation leads to lower FOXP3 expression in CD4+ T cells of patients with primary Sjögren's syndrome. Clin Immunol 148(2): 254-257.

XTL Biopharmaceuticals Ltd: "XTL Biopharmaceuticals Unveils Expanded hCDR1 Preclinical Data for the Treatment of Sjogrens Syndrome", prnewswire.com, Apr. 5, 2017, Retrieved from the Internet: URL: https://www.prnewswire.com/news-releases/xtl-biopharmaceuticals-unveils-expanded-hcdr1-preclinical-data-for-the-treatment-of-sjogrens-syndrome-618339393.html, accessed on Mar. 26, 2018; 4 pages.

XTL Biopharma (XTLB) Reports Additional Expanded hCDR1 Preclinical Data for the Treatment of Sjogren's Syndrome: "XTL Biopharma (XTLB) Reports Additional Expanded hCDR1 Preclinical Data for the Treatment of Sjogren's Syndrome", Streetinsider.com, Sep. 12, 2017, Retrieved from the Internet: URL: https://www.streetinsider.com/Corporate+News/XTL+Biopharma+%28XTLB%29+Reports+Additional +Expanded+hCDR1+Preclinical+Data+for+the+Treatment+of+Sjogrens+Syndrome/13287665.html, accessed on Mar. 26, 2018; 1 page.

\* cited by examiner

SEQUENCE LISTING

```
<160> NUMBER OF SEQ ID NOS: 7

<210> SEQ ID NO 1
<211> LENGTH: 19
<212> TYPE: PRT
<213> ORGANISM: Artificial Sequence
<220> FEATURE:
<223> OTHER INFORMATION: synthetic peptide

<400> SEQUENCE: 1

Gly Tyr Tyr Trp Ser Trp Ile Arg Gln Pro Pro Gly Lys Gly Glu Glu
1               5                   10                  15

Trp Ile Gly

<210> SEQ ID NO 2
<211> LENGTH: 19
<212> TYPE: PRT
<213> ORGANISM: Artificial Sequence
<220> FEATURE:
<223> OTHER INFORMATION: synthetic peptide

<400> SEQUENCE: 2

Ser Lys Gly Ile Pro Gln Tyr Gly Gly Trp Pro Trp Glu Gly Trp Arg
1               5                   10                  15

Tyr Glu Ile

<210> SEQ ID NO 3
<211> LENGTH: 18
<212> TYPE: PRT
<213> ORGANISM: Artificial Sequence
<220> FEATURE:
<223> OTHER INFORMATION: synthetic peptide

<400> SEQUENCE: 3

Tyr Tyr Trp Ser Trp Ile Arg Gln Pro Pro Gly Lys Gly Glu Glu Trp
1               5                   10                  15

Ile Gly

<210> SEQ ID NO 4
<211> LENGTH: 17
<212> TYPE: PRT
<213> ORGANISM: Artificial Sequence
<220> FEATURE:
<223> OTHER INFORMATION: synthetic peptide

<400> SEQUENCE: 4

Tyr Trp Ser Trp Ile Arg Gln Pro Pro Gly Lys Gly Glu Glu Trp Ile
1               5                   10                  15

Gly
```

```
<210> SEQ ID NO 5
<211> LENGTH: 18
<212> TYPE: PRT
<213> ORGANISM: Artificial Sequence
<220> FEATURE:
<223> OTHER INFORMATION: synthetic peptide

<400> SEQUENCE: 5

Gly Tyr Tyr Trp Ser Trp Ile Arg Gln Pro Pro Gly Lys Gly Glu Glu
1               5                   10                  15

Trp Ile

<210> SEQ ID NO 6
<211> LENGTH: 17
<212> TYPE: PRT
<213> ORGANISM: Artificial Sequence
<220> FEATURE:
<223> OTHER INFORMATION: synthetic peptide

<400> SEQUENCE: 6

Gly Tyr Tyr Trp Ser Trp Ile Arg Gln Pro Pro Gly Lys Gly Glu Glu
1               5                   10                  15

Trp

<210> SEQ ID NO 7
<211> LENGTH: 17
<212> TYPE: PRT
<213> ORGANISM: Artificial Sequence
<220> FEATURE:
<223> OTHER INFORMATION: synthetic peptide

<400> SEQUENCE: 7

Tyr Tyr Trp Ser Trp Ile Arg Gln Pro Pro Gly Lys Gly Glu Glu Trp
1               5                   10                  15

Ile
```

PEPTIDES FOR TREATING SJOGREN'S SYNDROME

FIELD OF THE INVENTION

The present invention generally relates to compositions and methods for the treatment of Sjogren's syndrome by synthetic peptides based on the sequence of the complementarity-determining region (CDR) 1 of an anti-DNA antibody.

BACKGROUND OF THE INVENTION

Sjögren's syndrome (SS), also termed Sicca syndrome), is a chronic, systemic, auto-immune disease, characterized by lymphocytic infiltration of exocrine glands. It can be manifested alone, as primary Sjogren's syndrome (pSS), or in addition to another autoimmune disease, as secondary Sjogren's syndrome (sSS). Clinical presentation varies, from mild classic symptoms such as dry eyes (xerophthalmia), dry mouth (xerostomia) and parotid gland enlargement, to severe systemic symptoms involving multiple organ systems such as arthritis, arthralgia, myalgia, pulmonary disease, gastrointestinal disease, neuropathy and lymphoma.

Worldwide, SS is estimated to affect millions of people. The female-to-male ratio of SS is 9:1. It can affect individuals of any age, but typically onset occurs in the fourth to fifth decade of life. In the United States, SS is estimated to be the second most common rheumatologic disorder. The prevalence of pSS varies from 0.01 up to 4.8%. This variability reflects differences in definition, application of diagnostic criteria, and differences in age groups. At present there are no effective treatments for the sicca symptoms apart from symptomatic therapy, while the severe systemic manifestations require immunosuppressive therapies.

hCDR1 (Edratide), having the sequence GYYWSWIRQPPGKGEEWIG (SEQ ID NO: 1), described in WO 02/067848 to the present inventor, is a peptide comprising a sequence based on the complementarity-determining region (CDR) no. 1 of the heavy chain of the human anti-DNA monoclonal antibody (mAb) 16/6Id. This mAb bears an idiotype which is clinically relevant to systemic lupus erythematosus (SLE). In hCDR1, the CDR sequence GYYWS is followed by the natural framework sequence of the heavy chain of the human 16/6Id mAb, with the exception that the natural leucine (L) residue of the mAb sequence was replaced by a glutamic acid residue (E) at position 15 of the peptide hCDR1. Although hCDR1 is based on the CDR1 of an anti-DNA monoclonal antibody, it does not bind either DNA, or anti-DNA antibodies, and was found to be a T cell epitope, rather than a B cell epitope. This peptide was shown to ameliorate serological and clinical disease manifestations of SLE in murine models via the down-regulation of auto-reactive T and B cells, pro-inflammatory cytokines and other pathogenic molecules, as well as up-regulating regulatory T cells and suppressive/regulatory molecules. Further, similar immunomodulatory effects of hCDR1 were demonstrated in-vitro on peripheral blood mononuclear cells (PBMCs) obtained from human lupus patients. Phase Ia and Ib clinical studies indicated that hCDR1 is safe and well tolerated in humans. Moreover, a Phase II clinical trial in SLE patients revealed beneficial effects of hCDR1 on several parameters (Urowitz et al., Lupus Science & Medicine 2015, Vol. 2:e000104).

The linkage between SLE and antibodies against double stranded DNA (anti-dsDNA) is clearly established and as shown by Gonzalez et al. (Journal of Immunological Methods, 2015, Vol. 427, pages 30-35), a positive predictive value (PPV) is obtained for SLE patients whose anti-dsDNA results are positive by combination of detection methods.

Sjogren's syndrome is an autoimmune disease believed to involve a combination of genetics and an environmental trigger. SS is similar to SLE with respect to some autoantibodies and clinical manifestations. While the exact cause of SS is not clear, no linkage between the disease and anti-dsDNA antibodies has been suggested or reported to date. Similarly, no linkage exists between anti-dsDNA antibodies and the autoimmune diseases rheumatoid arthritis (RA) and antiphospholipid syndrome (APS).

Thus, while SLE is primarily associated with anti-dsDNA antibodies, SS patients do not exhibit such antibodies, and are instead associated with the presence of anti-Ro antibodies and anti-La antibodies (Rao and Bowman, Ther. Adv. Musculoskel. Dis., 2013, Vol. 5(4), pages 234-249).

PCT application publication no. WO 2014/052393 relates to methods for the diagnosis and treatment of SS, based on genes which are differentially expressed in SS patients. For example, it was found that the gene encoding Interferon induced dynamin GTPase (MX1), but not the genes encoding interleukin-1β (IL-1β) and Tumor necrosis factor alpha (TNF-α), is overexpressed in SS patients compared to healthy control subjects. Willeke and coworkers have previously found that the number of peripheral blood mononuclear cells (PBMC) secreting TNF-α and IL-1β was significantly higher in patients with pSS than in controls (Ann. Rheum. Dis., 2003, Vol. 62, pages 359-362).

Maria et al. (Ann Rheu. Dis 2014, Vol. 73, pages 1052-1059), disclosed MX1 (termed MxA), as a clinically applicable biomarker for identifying systemic interferon (IFN) type I in pSS. It is shown that the IFN type I signature is present in over half of the pSS patients and identifies a subgroup with a higher disease activity.

It was previously reported that in human SS the level of B Lymphocyte Stimulator (BLyS) correlates with the level of autoantibodies (Mariette et al., Ann. Rheum. Dis. 2003, Vol. 62, pages 168-171). It has further been reported that in patients with pSS DNA hyper-methylation leads to lower expression of forkhead box P3 (FOXP3) in CD4+ T cells (Yu et al., Clin. Immunol. 2013, Vol. 148(2), pages 254-257; Liu et at, Lupus, 2008, Vol. 17, pages 34-39).

Maria et al. (Arthritis & Rheumatology, 2016, Vol. 68(7), pages 1688-1699) have recently suggested a role for elevated levels of the enzyme Indoleamine 2,3-dioxygenase (IDO) in the pathogenesis of pSS.

There is unmet medical need for agents and methods for treatment of SS in a safe, effective and specific manner.

SUMMARY OF THE INVENTION

The present invention provides methods for treating or ameliorating Sjogren's syndrome (SS) or at least one symptom associated with SS in human subjects. The present invention is based on the unexpected finding that a synthetic 19-amino-acid peptide, hCDR1, based on the CDR1 of a human antibody against DNA, is effective in treating SS, despite the fact that SS is not caused by or known to be associated with anti-DNA antibodies.

The present invention is based in part on the finding that peripheral blood immune cells isolated from SS patients, when incubated in-vitro with hCDR1, demonstrate statistically-significant changes in the expression of certain genes.

The present invention provides, in one aspect, a pharmaceutical composition comprising a peptide comprising the amino-acid sequence GYYWSWIRQPPGKGEEWIG set forth in SEQ ID NO: 1, an active fragment thereof, a salt thereof, a chemical derivative thereof, an analog thereof, or a conjugate thereof, for use in treating or ameliorating at least one symptom associated with SS.

In certain embodiments, the peptide comprises 19-40 consecutive amino acids. In certain embodiments, the peptide consists of 19-40 consecutive amino acids. In yet other embodiments, the peptide consists of 19-35, 19-30 or 19-25 consecutive amino acids.

In certain embodiments, the peptide consists of the amino-acid sequence set forth in SEQ ID NO: 1. In other embodiments, the peptide consists of an analog or chemical derivative of the amino acid sequence of SEQ ID NO: 1.

In certain embodiments, the chemical derivative is a peptide with modified C-terminus and/or N-terminus. In specific embodiments, the chemical derivative is a peptide with an amidated C-terminus. In other embodiments, the peptide comprises acylated N-terminus.

In some embodiments, an analog of the peptide of SEQ ID NO: 1 is provided comprising 1-4 substitutions, additions or deletions of amino acid residues with respect to SEQ ID NO: 1. In some specific embodiments, the analog comprises one amino acid addition, deletion or substitution to SEQ ID NO: 1.

According to some embodiments, the pharmaceutical composition comprises a peptide of 14-18 amino acid residues which is a fragment of the peptide of SEQ ID NO: 1. According to other embodiments, the fragment of SEQ ID NO: 1 consists of 17-18 consecutive amino acid residues. According to some specific embodiments, the peptide fragment is selected from the group consisting of:

```
                        SEQ ID NO: 3
YYWSWIRQPPGKGEEWIG;

SEQ ID NO: 4
YWSWIRQPPGKGEEWIG;

SEQ ID NO: 5
GYYWSWIRQPPGKGEEWI;

SEQ ID NO: 6
GYYWSWIRQPPGKGEEW;
and

SEQ ID NO: 7
YYWSWIRQPPGKGEEWI.
```

According to yet other embodiments, the pharmaceutical composition comprises at least one peptide consisting of a sequence selected from the group consisting of: SEQ ID NO: 1, SEQ ID NO: 3, SEQ ID No: 4, SEQ ID No: 5, SEQ ID No: 6, and SEQ ID No: 7, or of a salt thereof.

In certain embodiments, the conjugate comprises the peptide of SEQ ID NO: 1 or a derivative or analog thereof, covalently linked to an additional molecule. The peptide and the additional molecule may be covalently linked directly or through a spacer or linker. In certain embodiments, the additional molecule is selected from the group consisting of at least one additional peptide, a polypeptide or protein, a permeability enhancing moiety and a macromolecular carrier. The additional peptide may be same or different form the peptide of SEQ ID NO: 1 or its analog or derivative. According to some embodiments, the additional peptide comprises a sequence set forth in SEQ ID NO: 1. According to other embodiments, the additional peptide consist of the amino-acid sequence set forth in SEQ ID NO: 1. Each possibility represents a separate embodiment of the invention.

According to some embodiments, the pharmaceutical composition comprises between 50 μg to 1 mg of the peptide, its active fragment, salt, chemical derivative, analog or conjugate. According to yet other embodiments, the pharmaceutical composition comprises between 100 μg to 0.5 mg of the peptide, its active fragment, salt, chemical derivative, analog or conjugate.

The pharmaceutical composition can be administered, for example, in daily, weekly, biweekly, monthly or bimonthly regimens.

According to some specific embodiments, a pharmaceutical composition comprising between 100 μg to 0.5 mg of the peptide, its active fragment, salt, chemical derivative, analog or conjugate, is provided for a weekly administration.

According to some embodiments, the pharmaceutical compositions for use in treatment of at least one SS symptom, is formulated for administration in an amount sufficient to modulate the activity or expression of at least one gene associated with SS or with at least one SS symptom. According to some embodiments, the at least one gene is selected from the group consisting of: Interleukin 1 (IL-1), Tumor necrosis factor α (TNF-α), Interferon induced dynamin GTPase (MX1), B Lymphocyte Stimulator (BLyS), forkhead box P3 (FOXP3), Indoleamine 2,3-dioxygenase (IDO) and Transforming growth factor β (TGF-β). According to some embodiments, IL-1 is IL-1β. Each possibility represents a separate embodiment of the invention.

According to some specific embodiments, the modulation in the activity or expression of at least one gene is selected from the group consisting of: (i) downregulating the activity or expression of at least one gene coding for a cytokine selected from the group consisting of IL-1β, TNF-α, MX1 and BLyS, and (ii) upregulating the activity or expression of at least one gene coding for FOXP3, IDO, or TGF-β in immune cells of a human subject. Each possibility represents a separate embodiment of the invention.

According to some embodiments, the immune cells are peripheral blood lymphocytes (PBLs) or peripheral blood mononuclear cells (PBMCs).

The present invention provides, in another aspect, a method for treating or ameliorating at least one symptom associated with SS in a human subject in need of such treatment, the method comprising the step of administering to the subject a peptide comprising the amino-acid sequence set forth in SEQ ID NO: 1, an active fragment thereof, a salt thereof, a chemical derivative thereof, an analog or a conjugate thereof, thereby treating or ameliorating SS.

According to some embodiments, the method comprises administering to the subject a peptide selected from the group consisting of SEQ ID NO: 1, SEQ ID NO: 3, SEQ ID No: 4, SEQ ID No: 5, SEQ ID No: 6, and SEQ ID No: 7, or a chemical derivative, analog, salt or conjugate thereof.

According to some specific embodiments, the method comprises administering to the subject a peptide consisting of SEQ ID NO: 1 or a conjugate thereof.

In certain embodiments, the peptide is administered in an amount sufficient to modulate the activity or expression of at least one gene associated with SS or with at least one of its symptoms. According to some embodiments, the at least one gene is selected from the group consisting of: IL-1, TNF-α, MX1, BLyS, FOXP3, IDO and TGF-β. Each possibility represents a separate embodiment of the invention.

According to some specific embodiments, the modulation in the activity or expression of at least one gene is selected from the group consisting of: (i) downregulating the activity or expression of at least one gene coding for a cytokine selected from the group consisting of IL-1β, TNF-α, MX1 and BLyS, and (ii) upregulating the activity or expression of at least one gene coding for FOXP3, IDO, or TGF-β in immune cells of the subject. Each possibility represents a separate embodiment of the invention.

According to some embodiments, the method comprises administration of a pharmaceutical composition comprising between 100 μg to 0.5 mg of the peptide, its active fragment, salt, chemical derivative, analog or conjugate. Administration may be in any treatment regiment, for example, in daily, weekly, biweekly, monthly or bimonthly regimens.

According to some specific embodiments, the method comprises a weekly administration to a subject in need thereof, a pharmaceutical composition comprising between 100 μg to 0.5 mg of the peptide, its active fragment, salt, chemical derivative, analog or conjugate.

According to some embodiments, the immune cells are selected from PBLs and PBMCs.

In certain embodiments, the expression of IL-1 is downregulated. In certain embodiments, the IL-1 is IL-1β. In certain embodiments, the expression of TNF-α is downregulated. In certain embodiments, the expression of MX1 is downregulated. In certain embodiments, the expression of BLyS is downregulated. In certain embodiments, the expression of FOXP3 is upregulated. In certain embodiments, the expression of IDO is upregulated. In yet other embodiments, the expression of TGF-β is upregulated.

In certain embodiments, the at least one symptom associated with SS is selected from the group consisting of dry eyes, dry mouth, joint pain, joint swelling, joint stiffness, swollen salivary glands, skin rash, dry skin, vaginal dryness, persistent dry cough and prolonged fatigue. Each possibility represents a separate embodiment of the invention. In certain embodiments, the symptom is dry eyes. In certain embodiments, the symptom is dry mouth.

In certain embodiments, the subject is afflicted with primary Sjogren's syndrome (pSS). In certain embodiments, the subject is afflicted with secondary Sjogren's syndrome (sSS). In certain embodiments, the subject is further afflicted with systemic lupus erythematosus (SLE).

According to some embodiments, the subject eligible for treatment with the compositions of the present invention is identified by having high levels of MX1 (also termed MxA) protein in its blood or cells.

According to some embodiments, the subject in need of treatment belongs to a patient population having a high pSS disease activity, as determined by an elevated level of MX1 gene or protein expression.

The present invention further provides, in another aspect, a pharmaceutical composition comprising a peptide comprising the amino-acid sequence set forth in SEQ ID NO: 1, an active fragment thereof, a salt thereof, a chemical derivative thereof, an analog thereof or a conjugate thereof, for use in a method of modulating the activity or expression at least one gene associated with SS or with at least one symptom of the disease.

According to some embodiments, modulating the expression or activity is selected from: downregulating the activity or expression of at least one gene coding for a cytokine selected from the group consisting of IL-1β, TNF-α, MX1 and BLyS, and upregulating the activity or expression of at least one gene selected from the group consisting of: FOXP3, TGF-β and IDO, in peripheral blood lymphocytes of a SS patient.

The present invention further provides, in another aspect, a method of modulating the activity or expression of at least one gene associated with SS or with at least one of its symptoms, the method comprising the step of contacting the cells with a peptide comprising the amino-acid sequence set forth in SEQ ID NO: 1, an active fragment thereof, a salt thereof, a chemical derivative thereof, an analog thereof or a conjugate thereof, thereby downregulating the activity or expression of the at least one gene.

According to some embodiments, modulating the activity or expression comprises downregulating of at least one gene encoding for a cytokine selected from the group consisting of IL-1β, TNF-α, MX1 and BLyS, or upregulating the activity or expression of at least one gene selected from the group consisting of: FOXP3, TGF-β, or of IDO, in immune cells of a subject suffering from SS, the method comprising the step of contacting the cells with a peptide comprising or consisting of the amino-acid sequence set forth in SEQ ID NO: 1, an active fragment thereof, a salt thereof, a chemical derivative thereof, an analog thereof or a conjugate thereof, thereby downregulating the activity or expression of the at least one gene.

According to some embodiments, the immune cells contacted with a peptide comprising or consisting of the amino-acid sequence set forth in SEQ ID NO: 1, an active fragment thereof, a salt thereof, a chemical derivative thereof, an analog thereof or a conjugate thereof, are PBMCs. According to some specific embodiments, the immune cells are PBLs.

The immune cells may be contacted with the compositions and peptides of the invention using in-vitro, ex-vivo or in-vivo methods know in the art.

In certain embodiments, the PBLs or PBMCs are isolated from a SS patient. In certain embodiments, the peptide consists of the amino-acid sequence set forth in SEQ ID NO: 1.

Further embodiments and the full scope of applicability of the present invention will become apparent from the detailed description given hereinafter. However, it should be understood that the detailed description and specific examples, while indicating certain embodiments of the invention, are given by way of illustration only, since various changes and modifications within the spirit and scope of the invention will become apparent to those skilled in the art from this detailed description.

DETAILED DESCRIPTION OF THE INVENTION

Figure 1A:
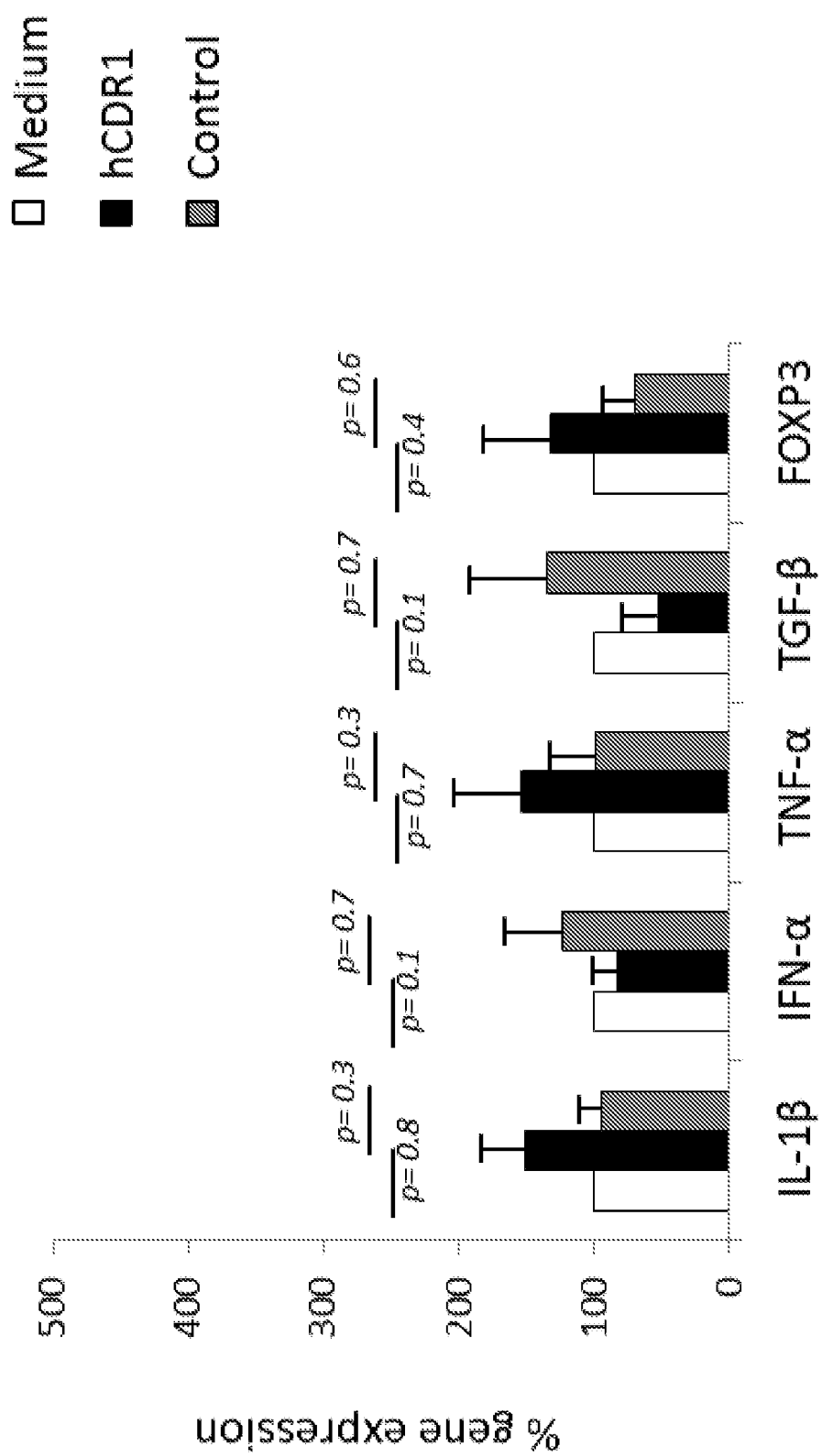
FIG. 1A is a bar graph illustrating the non-significant effects of hCDR1 on gene expression in cells of RA patients as compared to the effects of medium alone, and control scrambled peptide (SEQ ID NO: 2).

The present invention provides methods for treating or ameliorating at least one symptom associated with Sjogren's syndrome (SS) in human subjects. Specifically, it has been found that the 19-amino-acid synthetic peptide, hCDR1 (Edratide), based on the CDR1 of a human antibody against DNA, is beneficial and effective in treating SS.

hCDR1 was previously found effective in treating systemic lupus erythematosus (SLE), a disease strongly associated with high levels of anti-DNA antibodies but was not shown to be effective in treating other rheumatological auto-immune disorders, such as rheumatoid arthritis (RA) and antiphospholipid syndrome (APS). In contrast to SLE, the autoimmune diseases RA, APS and SS are not caused by or associated with anti-DNA antibodies, and therefore, none of these diseases is expected to respond to hCDR1 therapy. However, the present invention surprisingly demonstrates that hCDR1, while not being effective in RA and APS patients, is effective in treating SS. In addition, the Interferon induced dynamin GTPase (MX1) gene known to be elevated in SS patients was not previously reported to be associated with SLE, nor with the effects of hCDR1 therapy in SLE patients. Without being bound to any theory or mechanism, the findings presented herein suggest that hCDR1 is effective in SS therapy in ways different than its role in SLE therapy.

The present invention provides, in one aspect, a pharmaceutical composition comprising a peptide comprising the amino-acid sequence set forth in SEQ ID NO: 1, an active fragment thereof, a salt thereof, a chemical derivative thereof, an analog thereof or a conjugate thereof, for use in a method for treating or ameliorating at least one symptom associated with SS.

The present invention further provides, in another aspect, a method for treating or ameliorating SS or at least one symptom associated with SS in a human subject, the method comprising the step of administering to the subject a peptide comprising the amino-acid sequence set forth in SEQ ID NO: 1, an active fragment thereof, a salt thereof, a chemical derivative thereof, an analog thereof or a conjugate thereof, thereby treating SS.

The phrase "treating or ameliorating at least one symptom" as used herein refers to ameliorating and/or curing a disease as referred to herein, preventing progression of the disease or at least an amelioration of at least one symptom associated with the said disease.

The term "active fragment of SEQ ID NO: 1" as used herein refers to a peptide of 17 or 18 continuous amino-acids of SEQ ID NO: 1. In certain embodiments, the active fragment consists of 17 continuous amino-acids of SEQ ID NO: 1. In certain embodiments, the active fragment consists of 18 continuous amino-acids of SEQ ID NO: 1. In certain embodiments, the active fragment retains at least 50% of the activity of SEQ ID NO: 1. In certain embodiments, the active fragment of SEQ ID NO: 1 is selected from the sequences set forth in SEQ ID NOs: 3 to 7. Each possibility represents a separate embodiment of the invention.

Certain genes associated with SS are potentially modulated in response to the treatments of the present invention. According to some embodiments, at least one gene selected from the group consisting of: Interleukin 1β (IL-1β, NP_000567 for example), Tumor necrosis factor α (TNF-α, NP_000585 for example), Interferon induced dynamin GTPase (MX1, NP_002453 for example), B Lymphocyte Stimulator (BLyS, NP_006564 for example), forkhead box P3 (FOXP3, NP_054728 for example), transforming growth factor β (TGF-β, NP_000651 for example), and Indoleamine 2,3-dioxygenase (IDO, NP_002155 for example), is modulated.

According to some embodiments, administration of the peptides or pharmaceutical compositions included in the invention results in change in the expression or activity of at least one gene. In certain embodiments, the activity of IL-1 is downregulated. In certain embodiments, the expression of IL-1 is downregulated. In certain embodiments, the IL-1 is IL-1β. In certain embodiments, the activity of TNF-α is downregulated. In certain embodiments, the expression of TNF-α is downregulated. In certain embodiments, the activity of MX1 is downregulated. In certain embodiments, the expression of MX1 is downregulated. In certain embodiments, the expression of BLyS is downregulated. In certain embodiments, the expression of FOXP3 is upregulated. In certain embodiments, the expression of IDO is upregulated. In certain embodiments, the expression of TGF-β is upregulated.

In certain embodiments, the peptide is administered in an amount sufficient to (i) downregulate the activity and/or expression of at least one gene coding for a cytokine selected from the group consisting of: IL-1, TNF-α, MX1 and BLyS, or (ii) upregulate the activity and/or expression of at least one gene selected from: FOXP3, TGF-β, and IDO, in immune cells of the patient. Each possibility represents a separate embodiment of the invention. In certain embodiments, the immune cells are selected from PBMCs and PBLs.

In certain embodiments, the peptide consists of 19-40 consecutive amino acid residues. In certain embodiments, the peptide consists of 20-25, 25-30, 30-35 or 35-40 consecutive amino acid residues. In yet other embodiments, the peptide comprises 19-40 consecutive amino acid residues and at least one moiety which is not an amino acid residue.

According to some embodiments, the peptide comprises at least one modified, non-coded or non-natural amino acid residue.

According to some embodiments, the peptide comprises at least one modified bond.

According to some specific embodiments, the modified bond is an amide bond substituted with a bond selected from the group consisting of: urea bond, carbamate bond, sulfonamide bond, hydrazine bond, or any other covalent bond.

In certain embodiments, the peptide is a peptide derivative. According to some embodiments, the chemical derivative comprises at least one modification of the peptide's terminals According to some embodiments, the chemical derivative comprises modified C-terminus. According to some embodiments, the chemical derivative is an amide of the peptide's C-terminus. According to some embodiments, the chemical derivative comprises modified N-terminus, such as acylation of the N-terminus of the peptide.

In certain embodiments, the pharmaceutical composition comprises a conjugate of the peptide, analog, derivative or fragment of SEQ ID NO: 1 and at least one additional moiety. The conjugation of the peptide and the additional moiety may be directly according to some embodiments, or through a linker or spacer according to other embodiments. In certain embodiments, the additional molecule is selected from the group consisting of at least one additional peptide comprising or consisting of the amino-acid sequence set forth in SEQ ID NO: 1 and a macromolecular carrier. Each possibility represents a separate embodiment of the invention. In certain embodiments, the peptide of the conjugate consists of the amino-acid sequence set forth in SEQ ID NO: 1.

The term "linker" denotes a chemical moiety whose purpose is to link, covalently, a cell-permeability moiety and a peptide or peptidomimetic. The spacer may be used to allow distance between the permeability-enhancing moiety and the peptide, or it is a chemical bond of any type. Linker denotes a direct chemical bond or a spacer.

"Permeability" refers to the ability of an agent or substance to penetrate, pervade, or diffuse through a barrier, membrane, or a skin layer. A "cell permeability" or a "cell-penetration" moiety refers to any molecule known in the art which is able to facilitate or enhance penetration of molecules through membranes. Non-limitative examples include: hydrophobic moieties such as lipids, fatty acids, steroids and bulky aromatic or aliphatic compounds; moieties which may have cell-membrane receptors or carriers, such as steroids, vitamins and sugars, natural and non-natural amino acids, transporter peptides, nanoparticles and liposomes.

Any moiety, which is capable of improving the stability, solubility, permeability, or any other pharmacokinetic property of the peptide may be conjugated with the peptide of SEQ ID NO: 1, or with its fragment, derivative or analog, as long as it does not destroy its activity and do not confer antigenicity or adverse effects to the peptide conjugate.

In certain embodiments, the symptom which is treated or ameliorated with the pharmaceutical composition of the invention is selected from the group consisting of dry eyes, dry mouth, joint pain, joint swelling, joint stiffness, swollen salivary glands, skin rash, dry skin, vaginal dryness, persistent dry cough and prolonged fatigue. Each possibility represents a separate embodiment of the invention. In certain embodiments, the symptom is dry eyes. In certain embodiments, the symptom is dry mouth.

In certain embodiments, the subject treated with the pharmaceutical compositions of the present invention is afflicted with primary Sjögren's syndrome (pSS), i.e. afflicted with SS only. In certain embodiments, the patient is afflicted with secondary Sjögren's syndrome (sSS), i.e. afflicted with SS together with an additional autoimmune disease. In certain embodiments, the patient is further afflicted with systemic lupus erythematosus (SLE).

The present invention further provides, in another aspect, a pharmaceutical composition comprising a peptide comprising or consisting of the amino-acid sequence set forth in SEQ ID NO: 1, an active fragment thereof, a salt thereof, a chemical derivative thereof, an analog thereof or a conjugate thereof, for use in a method of modulating the expression or activity of at least one gene associated with SS, wherein modulating is selected from: (i) downregulating the activity and/or expression of at least one gene coding for a cytokine selected from the group consisting of: IL-1β, TNF-α, MX1 and BLyS, and (ii) upregulating the activity and/or expression of at least one gene selected from: FOXP3, TGF-β and IDO, in peripheral blood lymphocytes of a SS patient.

The present invention further provides, in another aspect, a method of modulating the expression or activity of at least one gene associated with SS, wherein modulating is selected from: (i) downregulating the activity and/or expression of at least one gene coding for a cytokine selected from the group consisting of: IL-1β, TNF-α, MX1 and BLyS, and (ii) upregulating the activity and/or expression of FOXP3, TGF-β, or IDO, in immune cells of a SS patient, the method comprising the step of contacting the cells with a peptide comprising the amino-acid sequence set forth in SEQ ID NO: 1, an active fragment thereof, a salt thereof, a chemical derivative thereof, an analog thereof, or a conjugate thereof, thereby modulating the activity and/or expression of the at least one gene.

In certain embodiments, the immune cells are PBLs or PBMCs. In certain embodiments, the PBLs or PBMCs are isolated from a SS patient. In certain embodiments, the peptide used consists of the amino-acid sequence set forth in SEQ ID NO: 1.

In certain embodiments, the hCDR1 peptide is a dual peptide comprising two copies of the hCDR1 peptide covalently linked to one another either directly or through a short linking chain. In certain embodiments, the hCDR1 peptide is a multi-synthetic peptide comprising multiple copies of the hCDR1 peptide covalently linked to one another either directly or through a short linking chain.

The present invention also includes chemical derivatives of the peptide hCDR1. The term "chemical derivative" refers to any peptide derived from an origin peptide in which one or more amino acids have been chemically derivatized by reaction of the functional side groups of the amino acids residues present in the origin peptide. Thus, a "chemical derivative" is a peptide that is derived from the sequences or peptides identified herein by one or more chemical steps. The term "chemical derivative" further contains additional chemical moieties not normally a part of the peptide and is encompassed by the invention as long as it retains at least a portion of the function of the peptide which permits its utility. For example, a chemical derivative may result from the reaction of an organic derivatizing agent capable of reacting with selected side chains or terminal residues of said peptide, and will retain at least a portion of the function of the peptide. Among these chemical derivatives, the amides are of particular interest, both amides of carboxyl groups at the C-terminus and amides of free carboxyl groups of aspartic or glutamic acid residues. Many such chemical derivatives and methods for making them are well known in the art. In certain embodiments, the chemical derivative of the peptide of the invention retains at least 50% of the function of the peptide. In certain embodiments, the chemical derivative of the peptide of the invention retains at least 75% of the function of the peptide. In certain embodiments, the chemical derivative of the peptide of the invention retains at least 90% of the function of the peptide. In certain embodiments, the conjugate of the peptide of the invention retains at least 50% of the function of the peptide. In certain embodiments, the conjugate of the peptide of the invention retains at least 75% of the function of the peptide. In certain embodiments, the conjugate of the peptide of the invention retains at least 90% of the function of the peptide.

Derivatives may include, for example, aliphatic esters of the carboxyl groups, amides of the carboxyl groups produced by reaction with ammonia or with primary or secondary amines, N-acyl derivatives of free amino groups of the amino acid residues formed by reaction with acyl moieties (e.g., alkanoyl or carbocyclic aroyl groups), or O-acyl derivatives of free hydroxyl group (e.g., that of seryl or threonyl residues) formed by reaction with acyl moieties.

The term "analog" indicates a molecule which has the amino acid sequence according to the invention except for one or more amino acid changes. Analogs according to the present invention may comprise also peptidomimetics. "Peptidomimetic" means that a peptide according to the invention is modified in such a way that it includes at least one non-coded residue or non-peptidic bond. Such modifications include, e.g., alkylation and more specific methylation of one or more residues, insertion of or replacement of natural amino acid by non-natural amino acids, replacement of an amide bond with another covalent bond. A peptidomimetic according to the present invention may optionally comprise at least one bond which is an amide-replacement bond such as urea bond, carbamate bond, sulfonamide bond, hydrazine bond, or any other covalent bond. The design of appropriate "analogs" may be computer assisted. Analogs are included in the invention as long as they remain pharmaceutically acceptable.

The amino acids used in this invention are those which are available commercially or are available by routine synthetic methods. Certain residues may require special methods for incorporation into the peptide, and either sequential, divergent or convergent synthetic approaches to the peptide sequence are useful in this invention. Natural coded amino acids and their derivatives are represented by three-letter codes according to IUPAC conventions. When there is no indication, the L isomer was used. The D isomers are indicated by "D" before the residue abbreviation.

Conservative substitutions of amino acids as known to those skilled in the art are within the scope of the present invention. Conservative amino acid substitutions include replacement of one amino acid with another having the same type of functional group or side chain, e.g., aliphatic, aromatic, positively charged, negatively charged. These substitutions may enhance oral bioavailability, penetration into the islets, targeting to specific beta cell populations, immunogenicity, and the like. One of skill will recognize that individual substitutions, deletions or additions to a peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

The following six groups each contain amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Also included in the scope of the invention are salts of the hCDR1 peptide. As used herein, the term "salts" refers to both salts of carboxyl groups and to acid addition salts of amino groups of the peptide molecule. Salts of a carboxyl group may be formed by means known in the art and include inorganic salts, for example, sodium, calcium, ammonium, ferric or zinc salts, and the like, and salts with organic bases such as those formed for example, with amines, such as triethanolamine, arginine, or lysine, piperidine, procaine, and the like. Acid addition salts include, for example, salts with mineral acids such as, for example, hydrochloric acid or sulfuric acid, and salts with organic acids, such as, for example, acetic acid or oxalic acid. Such chemical derivatives and salts are preferably used to modify the pharmaceutical properties of the peptide insofar as stability, solubility, etc., are concerned.

Peptide derivatives, salts and analogs are included in the invention as long as they remain pharmaceutically acceptable, i.e., they do not destroy the activity of the peptide, do not confer toxic properties on compositions containing it, and do not adversely affect the immunogenic properties thereof.

According to a further embodiment of the present invention, one or more hCDR1 peptides may be conjugated to a suitable macromolecular carrier or may be polymerized or branched through a suitable linker, such as a Lysine amino acid residue. Conjugation or polymerization may be performed using any method know in the art, including but not limited to conjugation in the presence of glutaraldehyde.

In certain embodiments, the peptides, derivatives, analogs, fragments, polymers thereof or their conjugates with suitable macromolecular carriers or other moieties, are administered to patients in a form that insures their bioavailability, making them suitable for treatment.

The present invention also contemplates pharmaceutical formulations or compositions for human medical use.

According to some embodiments of the present invention, a pharmaceutical composition is provided comprising at least one peptide or a fragment, salt, derivative or analog thereof. In such pharmaceutical compositions and medicament formulations, the active agent is preferably utilized together with one or more pharmaceutically acceptable carrier(s) and optionally any other therapeutic ingredients. The carrier(s) must be pharmaceutically acceptable in the sense of being compatible with the other ingredients of the formulation and not unduly deleterious to the recipient thereof. The active agent is provided in an amount effective to achieve the desired pharmacological effect, as described above, and in a quantity appropriate to achieve the desired dose.

The molecules of the present invention as active ingredients are dissolved, dispersed or admixed in an excipient that is pharmaceutically acceptable and compatible with the active ingredient as is well known. Suitable excipients are, for example, water, saline, phosphate buffered saline (PBS), dextrose, glycerol, ethanol, or the like and combinations thereof. Other suitable carriers are well known to those skilled in the art. In addition, if desired, the composition can contain minor amounts of auxiliary substances such as wetting or emulsifying agents, pH buffering agents.

Typically, the molecules of the present invention will be suspended in a sterile saline solution for therapeutic uses. The pharmaceutical compositions alternatively may be formulated to control release of active ingredient (molecule comprising the antigen-binding portion of an antibody) or to prolong its presence in a patient's body. Numerous suitable drug delivery systems are known and include, e.g., implantable drug release systems, hydrogels, hydroxymethylcellulose, microcapsules, liposomes, microemulsions, microspheres, and the like. Controlled release preparations can be prepared through the use of polymers to complex or adsorb the molecule according to the present invention. For example, biocompatible polymers include matrices of poly (ethylene-co-vinyl acetate) and matrices of a polyanhydride copolymer of a stearic acid dimer and sebaric acid. The rate of release of the molecule according to the present invention from such a matrix depends upon the molecular weight of the molecule, the amount of the molecule within the matrix, and the size of dispersed particles.

Any suitable route of administration is encompassed by the invention, including parenteral and enteral routes. Administration may be performed using oral, intravenous, subcutaneous, intraarticular, intramuscular, inhalation, intranasal, intrathecal, intraperitoneal, intradermal, transdermal, intra-arterial, intralesion, topical or other known routes. In certain embodiments, the composition is administered by a parenteral route such as an injection. in some specific embodiments, the composition is administered by subcutaneous administration.

It will be apparent to those of ordinary skill in the art that the therapeutically effective amount of the molecule according to the present invention will depend, inter alia upon the administration schedule, the unit dose of molecule administered, whether the molecule is administered in combination with other therapeutic agents, the immune status and health of the patient, the therapeutic activity of the molecule administered and the judgment of the treating physician. As used herein, a "therapeutically effective amount" refers to the amount of a molecule required to alleviate one or more symptoms associated with a disorder being treated over a period of time.

Although an appropriate dosage of a molecule of the invention varies depending on the administration route, type of molecule (peptide, salt, derivative, analog) age, sex, or conditions of the patient, it will be determined by the physician in the end. In the case of parenteral administration, the dosage of the hCDR1 peptide, and its fragments, derivatives, salts, analogs, or conjugates for treating SS, can generally be between about 5 µg to 5 mg. According to some embodiments the daily dose is between 50 µg to 1 mg. According to yet other embodiments, the daily dose is between 100 µg to 0.5 mg. The peptide can be administered, for example, in daily, weekly, biweekly, monthly or bimonthly regimens.

The invention still further relates to the use of the hCDR1 peptide, active fragment thereof, salt thereof, chemical derivative thereof, analog thereof, conjugate thereof or polymer thereof for the preparation of a medicament for treatment of SS.

The present invention further provides, in another aspect, a peptide comprising the amino-acid sequence set forth in SEQ ID NO: 1, an active fragment thereof, a salt thereof, a chemical derivative thereof or a conjugate thereof, for use in treating or ameliorating at least one symptom associated with SS in a patient.

The present invention further provides, in another aspect, a peptide comprising the amino-acid sequence set forth in SEQ ID NO: 1, an active fragment thereof, a salt thereof, a chemical derivative thereof or a conjugate thereof, for use in downregulating the activity and/or expression of at least one gene coding for a cytokine selected from the group consisting of IL-1β, TNF-α, MX1 and BLyS, or for use in upregulating the activity and/or expression of FOXP3, TGF-β or IDO, in peripheral blood lymphocytes of a SS patient.

In certain embodiments, the peptide contacts the lymphocytes ex-vivo. In certain embodiments, the lymphocytes contacted ex-vivo with the peptide are administered to the SS patient.

The peptide of present invention may be produced by any method known in the art, including recombinant and synthetic methods. Synthetic methods include exclusive solid phase synthesis, partial solid phase synthesis, fragment condensation, or classical solution synthesis. Solid phase peptide synthesis procedures are well known to one skilled in the art. In some embodiments, synthetic peptides are purified by preparative high performance liquid chromatography and the peptide sequence is confirmed via amino acid sequencing by methods known to one skilled in the art.

In some embodiments, recombinant protein techniques known in the art are used to generate the peptide of the present invention. In some embodiments, recombinant protein techniques are used for generation of relatively long polypeptides (typically longer than 20 amino acids).

While the present invention has been described with reference to certain embodiments, it will be understood by those skilled in the art that various changes may be made and equivalents may be substituted without departing from the scope of the present invention. In addition, many modifications may be made to adapt a particular situation or material to the teachings of the present invention without departing from its scope. Therefore, it is intended that the present invention not be limited to the particular embodiment disclosed, but that the present invention will include all embodiments falling within the scope of the appended claims.

The following examples are presented in order to more fully illustrate some embodiments of the invention. It should, in no way, be construed, however, as limiting the broad scope of the invention.

EXAMPLES

Peptides

Table 1 lists some of the peptides of the present invention.

TABLE 1

| SEQ ID NO: | Amino acid sequence | Length | Comments |
|---|---|---|---|
| 1 | GYYWSWIRQPPGKGEEWIG | 19 | hCDR1, Edratide |
| 2 | SKGIPQYGGWPWEGWRYEI | 19 | Scrambled sequence of hCDR1. Control peptide |
| 3 | YYWSWIRQPPGKGEEWIG | 18 | fragment of hCDR1 |
| 4 | YWSWIRQPPGKGEEWIG | 17 | fragment of hCDR1 |
| 5 | GYYWSWIRQPPGKGEEWI | 18 | fragment of hCDR1 |
| 6 | GYYWSWIRQPPGKGEEW | 17 | fragment of hCDR1 |
| 7 | YYWSWIRQPPGKGEEWI | 17 | fragment of hCDR1 |

Example 1

Effects of hCDR1 on Peripheral Blood Lymphocytes In-Vitro

Experimental Design

5×10$^6$/mL peripheral blood mononuclear cells (PBMCs) obtained from blood samples of rheumatoid arthritis (RA) patients, anti-phospholipid syndrome patients (APS) and SS patients were incubated in-vitro in: medium alone, medium containing 25 µg/mL hCDR1 (SEQ ID NO: 1), or medium containing 25 µg/mL of control scrambled peptide (SEQ ID NO: 2). Following 48 hours of incubation, cells were collected and mRNA was prepared from all samples. The expression of various genes was determined using real-time RT-PCR. The control peptide has the same amino acid residues as SEQ ID NO:1 in a scrambled order.

Figure 1B:
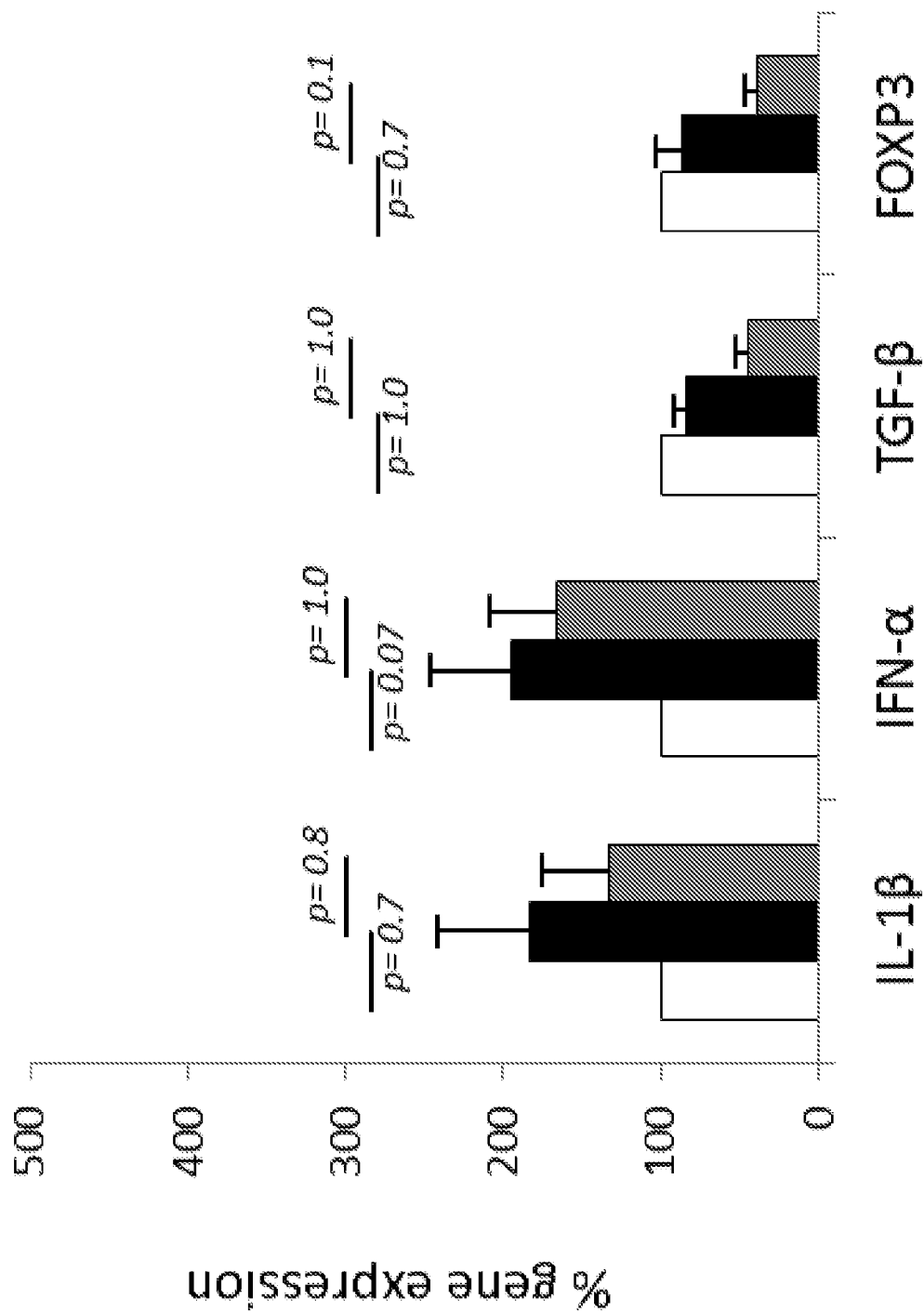
FIG. 1B is a bar graph illustrating the non-significant effects of hCDR1 on gene expression in cells of patients with APS as compared to the effects of medium alone and to control scrambled peptide.

No significant effects could be observed on gene expression of pathogenic cytokines when PBMCs of patients with either rheumatoid arthritis or anti-phospholipid syndrome were treated with hCDR1 (FIGS. 1A and 1B, respectively) compared to medium alone or compared to the control peptide. These findings suggest that the peptide hCDR1 (SEQ ID NO: 1) has no demonstrable immunomodulatory effect on the PBMCs of patients with rheumatoid arthritis or anti-phospholipid syndrome.

Figure 2:
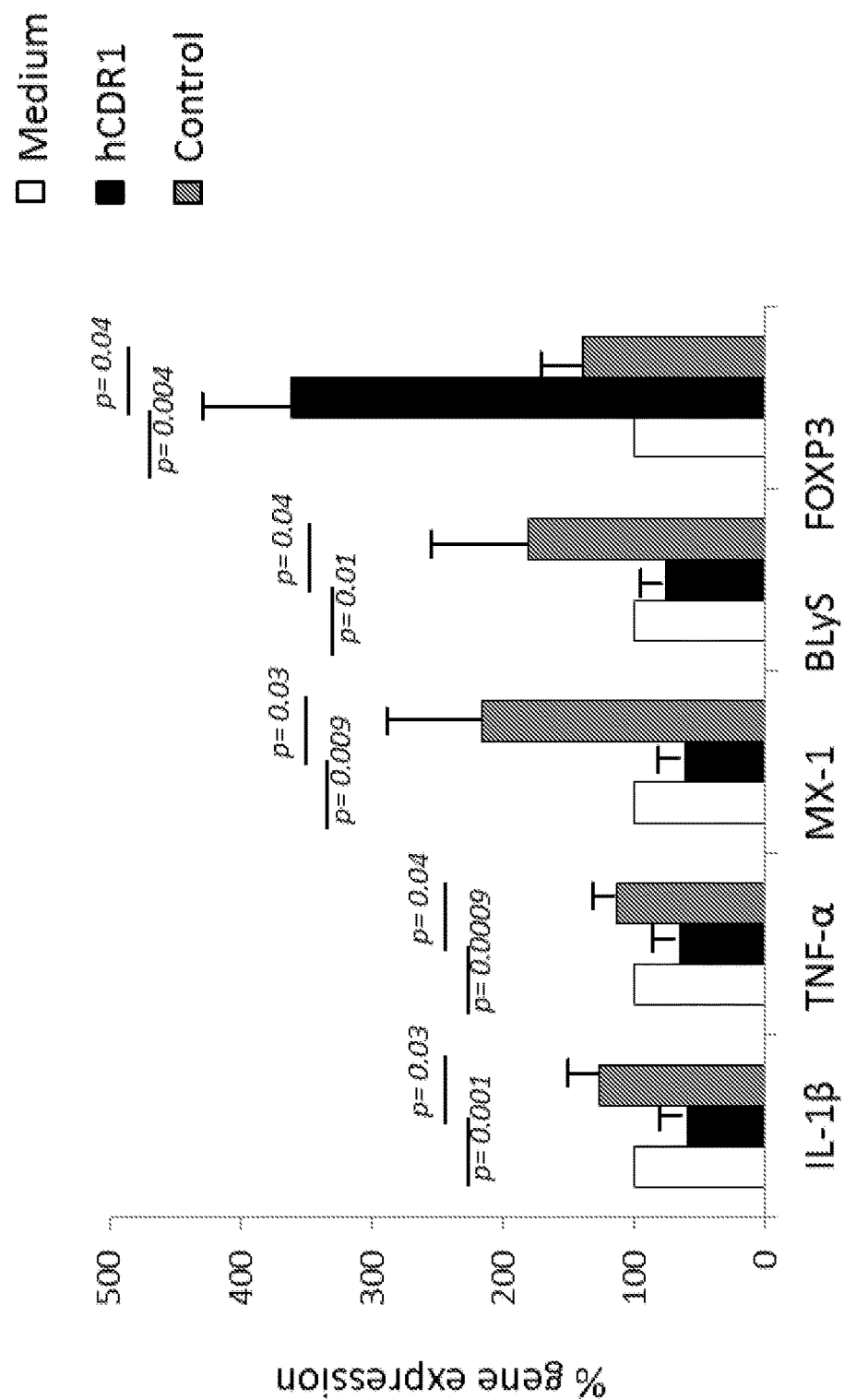
FIG. 2 is a bar graph illustrating the significant effects of hCDR1 on gene expression of IL-1β, TNFα, MX1, BLyS and FOXP3, in cells of patients with SS as compared to the effects of medium alone and control scrambled peptide.

In contrast, the results indicate that incubation of PBMCs of SS patients with hCDR1 results in a significant reduction of gene expression (down regulation) of 3 cytokines (IL-1β, TNF-α and MX1) considered to be pathogenic in SS (FIG. 2).

The results further indicate that incubation of PBMCs of SS patients with hCDR1 results in a significant reduction of gene expression (down regulation) of the BLyS gene, and in a significant increase of gene expression (up regulation) of the FOXP3 gene (FIG. 2).

The failure of hCDR1 to beneficially manipulate genes in cells derived from patients with either rheumatoid arthritis or anti-phospholipid syndrome, which similar to SS and in contrast to SLE are not associated with the presence of anti-DNA antibodies, stresses the surprising nature of the findings described herein. SS is similar to SLE in many of the manifestations, as well as in the fact that many SLE patients possess anti-Ro and anti-La antibodies which are the hallmark of SS. Table 2 and FIG. 2 summarizes the results obtained in PBMCs of SS patients when treated with the peptide of SEQ ID NO: 1 in comparison to treatment with a scrambled peptide and medium alone.

TABLE 2

Percent responders exhibiting gene expression modulation

| | | Responders/Total* | |
|---|---|---|---|
| Gene | Modulation by hCDR1 | hCDR1 compared to medium | hCDR1 compared to control peptide |
| IL-1β | Downregulation | 12/14 (86%) | 8/13 (61.5%) |
| TNF-α | Downregulation | 11/14 (78.5%) | 8/13 (61.5%) |
| MX1 | Downregulation | 10/13 (77%) | 10/13 (77%) |
| BLyS | Downregulation | 12/17 (70.5%) | 6/12 (50%) |
| FOXP3 | Upregulation | 12/16 (75%) | 7/12 (58%) |
| IDO | Upregulation | 13/16 (81%) | 9/13 (69%) |
| TGF-β | Upregulation | 12/17 (70.5%) | 8/11 (72.7%) |

*Responders represents individual SS patients whose isolated PBMCs showed significant change in the expression of the specified gene. Total includes all patients used in the assay (responders and non-responders).

Example 2

Figure 3A:
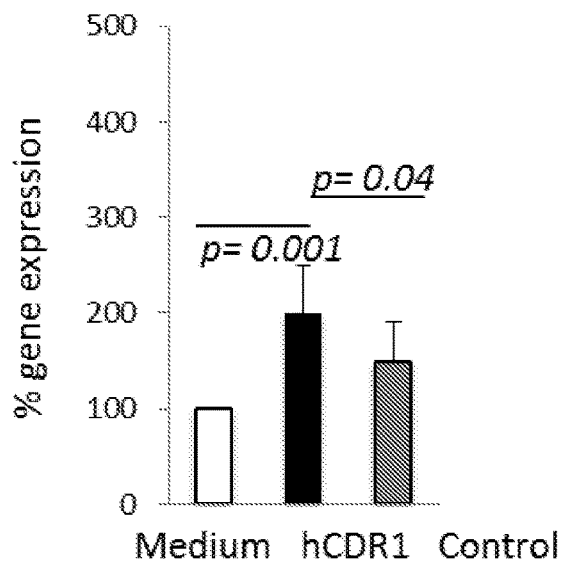
FIGS. 3A and 3B are bar graphs illustrating the effects of hCDR1, medium alone and control scrambled peptide on IDO gene expression in cells of subjects with pSS (3A) and RA (3B).
Figure 3B:
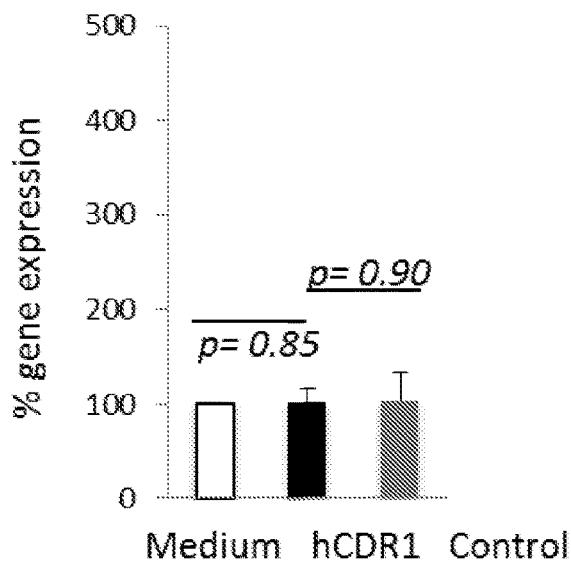

Indoleamine 2,3-Dioxygenase (IDO) and Transforming Growth Factor β (TGF-β) Up-Regulation by hCDR1
Experimental Design PBMCs of patients with pSS were isolated and incubated in vitro for 48 hours in the presence of medium, hCDR1 (SEQ ID NO: 1) or a control scrambled peptide (SEQ ID NO: 2). Thereafter, RNA was extracted from the cells and gene expression was determined by real-time RT-PCR. FIG. 3A demonstrates that in-vitro incubation of hCDR1 with PBMCs of patients with pSS up-regulated significantly the expression of the IDO gene as compared to its expression following cell incubation with medium alone or in the presence of the control peptide. This effect is specific to patients with pSS because, as shown in FIG. 3B, hCDR1 did not affect significantly the expression of IDO in PBMCs of subjects with RA.

Similar results were obtained with the expression of the gene for TGF-β, which was significantly up-regulated in PBMCs isolated from SS patients, in response to their incubation with hCDR1 ($p=0.012$ and $p=0.028$ for cells incubated with hCDR1 as compared to cells incubated with medium alone and control peptide, respectively), but not with medium alone or control scrambled peptide.

Figure 3C:
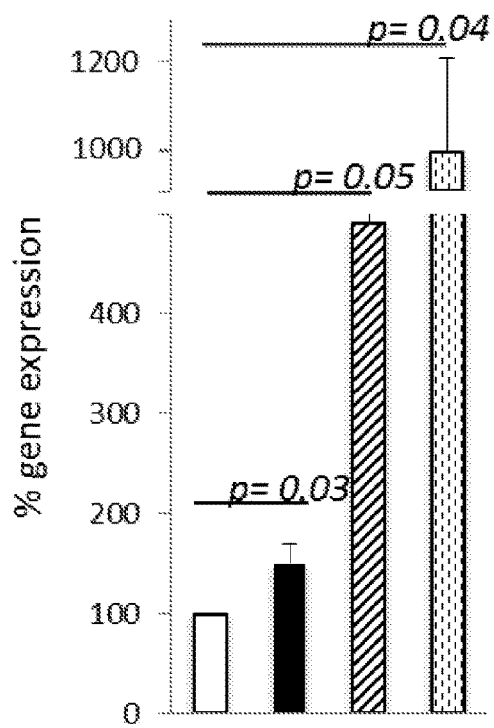
FIG. 3C is a bar graph illustrating the effects of medium alone, hCDR1, and combinations of hCDR1 with IL-1β or with IFN-α on expression of the IDO gene.

Since both IL-1β and IFN-α were reported to increase the production and expression of IDO, the effects of the addition of recombinant IL-1β or IFN-α to cultures of PBMCs with hCDR1 on IDO gene expression were further tested. As shown in FIG. 3C, the addition of either of these cytokines increased IDO gene expression to levels much higher than those determined in the presence of hCDR1 alone.

Figure 3D:
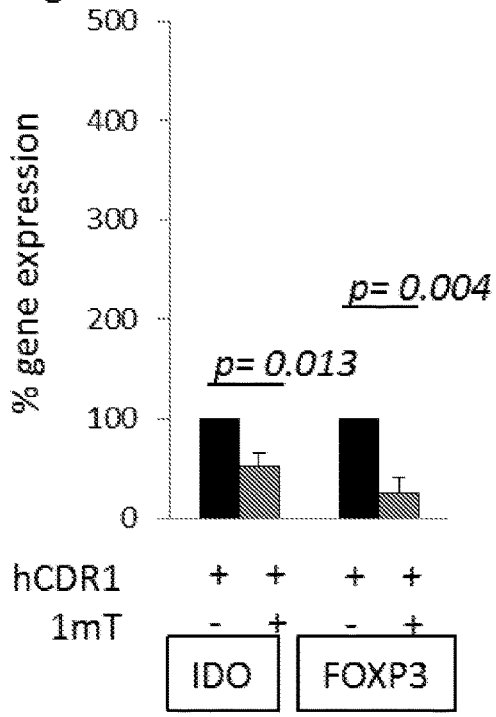
FIG. 3D is a bar graph illustrating the effects of hCDR1 alone, or a combination of hCDR1 and the IDO inhibitor 1 mT, on the expression of IDO and FOXP3 genes.

In order to check whether the hCDR1 induced up-regulated expression of IDO contributes to the beneficial effects of hCDR1 on the cytokine balance in pSS patients, the IDO inhibitor 1-methyl-D-tryptophan (1 mT) was added to cultures of hCDR1 with PBMCs of pSS patients. The effect of IDO inhibition on the expression of the suppressive master gene FOXP3, that is expressed on functional T regulatory cells, was tested. FIG. 3D demonstrates that the addition of 1 mT to PBMC cultures with hCDR1 led to a significant decrease in the IDO gene expression. Furthermore, inhibition of IDO interfered with the ability of hCDR1 to up-regulate the expression of FOXP3 and resulted in a significant down-regulation of FOXP3. These results suggest that the hCDR1 induced up-regulation of functional regulatory T cells that express FOXP3 is at least partially via the IDO pathway.

Example 3

Experimental Design—Animal Model of SS

Various mouse models have been developed aiming to establish the symptoms of SS in vivo. Park et al. divided the models into three categories of spontaneous, genetically engineered, and experimentally induced development of SS-like disease (Curr. Pharm. Des., 2015, Vol. 21, pages 2350-2364).

In the present experiment, BALB/c mice, or similar model animals, are immunized by repeated intraperitoneal injections of short peptides from 60-kDa Ro antigen, and develop anti-Ro antibodies, salivary gland lymphocyte infiltrates, and salivary dysfunction that is highly reminiscent of human SS (Scofield et al., 2005, J. Immunol., Vol. 175, pages 8409-8414). Concomitant with the immunization, mice are injected subcutaneously (s.c.) with vehicle alone (PBS), 25-50 µg of control peptide in PBS or 25-50 µg of hCDR1 in PBS. Before, during and following treatment the mice are monitored for changes in at least one of the symptoms of SS, such as leukocyte infiltration into the exocrine glands, xerostomia (dry mouth), keratoconjunctivitis sicca (dry eyes), fatigue, arthritis, Raynaud's phenomenon (reduced blood flow), and/or a variety of musculoskeletal, gastrointestinal, hepatobiliary, hematologic, vascular, dermatologic, renal and nervous systems dysfunctions.

Example 4

Experimental Design—Clinical Trial—Phase I

A Phase I Pilot-Study with hCDR1 (Edratide) for the Treatment of pSS.

Primary outcome measures—evaluation of the safety (type and number of adverse events and serious adverse events) of Edratide in patients with pSS. Secondary outcome measures—examination of the therapeutic effects of Edratide in patients with pSS. Other outcome measures—study the general health changes and improvement of sicca-symptoms.

Inclusion criteria: diagnosis of pSS. Exclusion criteria: relevant cardiac, pulmonary, neurologic or psychiatric disease; pregnant or breast-feeding. Gender: both, ages: 18 years to 75 years, accepts healthy volunteers: no.

Example 5

Experimental Design—Clinical Trial—Phase II

A multi-national, multi-center, randomized, double-blind, placebo-controlled, multiple-dose, parallel group study to assess the efficacy, tolerability and safety of Edratide for subcutaneous injection in Sjogren's syndrome.

Original primary outcome measures—improvement of disease activity score. Tested material: Edratide; 0.25 mg, 0.5 mg, 1.0 mg, and 2.5 mg injection once weekly.

Inclusion criteria: willing and able to give written informed consent; between the ages of 18 and 65 years (inclusive); pSS patients with moderate, active disease; women of child-bearing potential must practice a medically acceptable method of contraception; must understand the requirements of the study and agree to comply with the study protocol. Exclusion criteria: any condition which the investigator feels may interfere with participation in the study; subjects having a history of chronic infection; subjects with a history of immunodeficiency syndrome or malignancy; subjects who received any investigational medication within 3 months prior to randomization; subjects treated with any cytotoxic agents in the 3 months prior to randomization. Gender: both; ages: 18 years to 65 years; accepts healthy volunteers: no.

The invention claimed is:

1. A method for treating Sjogren's Syndrome (SS) in a human subject, the method comprising the step of administering to the subject having SS a pharmaceutical composition comprising at least one peptide selected from the group consisting of:
   a peptide having an amino-acid sequence of SEQ ID NO: 1;
   an active fragment of a peptide of SEQ ID NO: 1 selected from the group consisting of: SEQ ID NO: 3, SEQ ID NO: 4, SEQ ID NO: 5, SEQ ID NO: 6, and SEQ ID NO: 7;
   a salt of a peptide of SEQ ID NO: 1, SEQ ID NO: 3, SEQ ID NO: 4, SEQ ID NO: 5, SEQ ID NO: 6, or SEQ ID NO: 7;
   a chemical derivative of a peptide of SEQ ID NO: 1, SEQ ID NO: 3, SEQ ID NO: 4, SEQ ID NO: 5, SEQ ID NO: 6, or SEQ ID NO: 7, wherein the chemical derivative is a C-terminus modified with an amide and an acylated N-terminus; and
   a conjugate of a peptide of SEQ ID NO: 1, SEQ ID NO: 3, SEQ ID NO: 4, SEQ ID NO: 5, SEQ ID NO: 6, or SEQ ID NO: 7.

2. The method of claim 1, wherein the peptide consists of the amino-acid sequence set forth in SEQ ID NO: 1.

3. The method of claim 1, wherein the peptide is an active fragment selected from the group consisting of:

YYWSWIRQPPGKGEEWIG;   SEQ ID NO: 3

YWSWIRQPPGKGEEWIG;   SEQ ID NO: 4

GYYWSWIRQPPGKGEEWI;   SEQ ID NO: 5

GYYWSWIRQPPGKGEEW;   SEQ ID NO: 6
and

YYWSWIRQPPGKGEEWI.   SEQ ID NO: 7

4. The method of claim 1, wherein the conjugate comprises an additional molecule covalently attached to the peptide directly or by a linker, wherein the additional molecule is selected from the group consisting of: at least one additional peptide, a polypeptide, a protein, a permeability enhancing moiety and a macromolecular carrier.

5. The method of claim 1, wherein the subject is afflicted with pSS.

6. The method of claim 5, wherein the subject is afflicted with high pSS disease activity as determined by elevated level of MX1 gene or protein expression.

7. The method of claim 1, wherein the peptide is administered in an amount sufficient to modulate the expression or activity of at least one gene associated with Sjogren's syndrome (SS), in immune cells of the subject.

8. The method of claim 7, wherein modulation of expression or activity of at least one gene is selected from: (i) downregulating the activity or expression of at least one gene coding for a cytokine selected from the group consisting of interleukin-1β (IL-1β), Tumor necrosis factor alpha (TNF-α), Interferon induced dynamin GTPase (MX1) and B Lymphocyte Stimulator (BLyS); and (ii) upregulating the activity or expression of forkhead box P3 (FOXP3), Transforming growth factor beta (TGF-β) or Indoleamine 2,3-dioxygenase (IDO).

9. The method of claim 7, wherein the immune cells are peripheral blood lymphocytes (PBLs) or peripheral blood mononuclear cells (PBMCs).

10. The method of claim 1, wherein the pharmaceutical composition comprises between 50 μg to 1 mg of the peptide, its active fragment, salt, chemical derivative, or conjugate thereof.

11. The method of claim 10, comprising weekly administration of said pharmaceutical composition.

* * * * *